(12) United States Patent
Behera et al.

(10) Patent No.: US 11,607,286 B2
(45) Date of Patent: Mar. 21, 2023

(54) STERILE COVER FOR A MIXED REALITY (MR) DEVICE

(71) Applicant: HCL Technologies Limited, New Delhi (IN)

(72) Inventors: Sanjeeb Kumar Behera, Karnataka (IN); Karthik Balasubramanian, Tamil Nadu (IN); Dipumon Ayyanchira Mani, Karnataka (IN)

(73) Assignee: HCL Technologies Limited, New Delhi (IN)

( * ) Notice: Subject to any disclaimer, the term of this patent is extended or adjusted under 35 U.S.C. 154(b) by 256 days.

(21) Appl. No.: 17/032,906

(22) Filed: Sep. 25, 2020

(65) Prior Publication Data

US 2022/0015854 A1    Jan. 20, 2022

(30) Foreign Application Priority Data

Jul. 18, 2020   (IN) .............................. 202011030718

(51) Int. Cl.
| | | |
|---|---|---|
| *A61B 46/10* | (2016.01) | |
| *A61B 34/00* | (2016.01) | |
| *A61B 46/00* | (2016.01) | |
| *A61B 90/00* | (2016.01) | |
| *A61B 90/50* | (2016.01) | |

(52) U.S. Cl.
CPC .............. *A61B 46/10* (2016.02); *A61B 34/25* (2016.02); *A61B 46/40* (2016.02); *A61B 90/36* (2016.02); *A61B 2090/364* (2016.02); *A61B 2090/502* (2016.02)

(58) Field of Classification Search
CPC ......... A61B 46/10; A61B 46/40; A61B 34/25; A61B 90/36; A61B 2090/364; A61B 2090/502

USPC ........................................................... 428/68
See application file for complete search history.

(56) References Cited

U.S. PATENT DOCUMENTS

| | | | |
|---|---|---|---|
| 5,949,388 A | 9/1999 | Atsumi et al. | |
| 6,019,468 A * | 2/2000 | Altemare, Jr. | ........... G02C 3/02 351/158 |
| 6,318,864 B1 | 11/2001 | Fukaya et al. | |
| 2008/0250538 A1* | 10/2008 | Saladino | ................ G02C 5/008 2/10 |
| 2009/0216070 A1* | 8/2009 | Hunt | ..................... A61M 21/02 463/31 |
| 2015/0272784 A1* | 10/2015 | Padovani | ................ A61F 9/029 2/439 |

FOREIGN PATENT DOCUMENTS

| | | | |
|---|---|---|---|
| CN | 203428185 U | * | 2/2014 |
| JP | 2012023495 A | | 2/2012 |
| JP | 2017068105 A | | 4/2017 |

* cited by examiner

*Primary Examiner* — Mark Edwards (57) ABSTRACT

Disclosed is a sterile cover (100) for a Mixed Reality (MR) device (101). The sterile cover (100) may comprise a first case (102) arranged for covering a front side of the MR device (101). The first case (102) may comprise a hard case with an embedded clear layer (114) for covering a glass area of the front side of the MR device (101). The sterile cover (100) may further comprise a second case (104). The second case (104) may be arranged for covering a headband side of the MR device (101). The second case (104) may comprise a stretchable case for allowing a flexible adjustment of the headband side of the MR device (101) within the second case (104).

8 Claims, 9 Drawing Sheets

STERILE COVER FOR A MIXED REALITY (MR) DEVICE

CROSS-REFERENCE TO RELATED APPLICATIONS AND PRIORITY

The present application claims priority from Indian Patent Application No. 202011030718 filed on 18 Jul. 2020, the entity of which is hereby incorporated by reference.

TECHNICAL FIELD

The present disclosure in general relates to the field of protection means for devices. More particularly, the present invention relates to a sterile cover for a Mixed Reality (MR) device.

BACKGROUND

Mixed Reality (MR) devices such as Microsoft HoloLens, Magic Leap 1 Lightware, headsets are being used in number of application areas because of technical advantages offered by such MR devices. One of a significant application area is medical field, as virtually assisted surgeries are fast becoming a reality in medical industry due to enhanced accuracy and improved guidance. Several institutions are experimenting with the technology of mixed reality for assisting medical surgeries. MR devices may potentially be considered as future of surgical aid and hence are highly researched subject area.

The virtually assisted surgeries may become a common practice in future however, one main area of concern is sterility of the MR devices in case of repeated use in Operating Room (OR). Typically, in medical surgeries, sterility is given a heavy weightage and therefore, maintaining sterility of the MR devices becomes automatically important. Though advantages are many, however, maintaining sterility of the MR devices is very challenging, as the MR devices exposed to surgical environment, may lead to contamination, and physical damage of the MR devices as they are not designed for use in the OR for surgical assistance.

SUMMARY

Before the present sterile cover for a Mixed Reality (MR) device is described, it is to be understood that this application is not limited to the particular systems, and methodologies described, as there can be multiple possible embodiments which are not expressly illustrated in the present disclosure. It is also to be understood that the terminology used in the description is for the purpose of describing the particular versions or embodiments only, and is not intended to limit the scope of the present application. This summary is provided to introduce concepts related to the cover for a Mixed Reality (MR) device. This summary is not intended to identify essential features of the claimed subject matter nor is it intended for use in determining or limiting the scope of the claimed subject matter.

In one implementation, a sterile cover for a Mixed Reality (MR) device may be illustrated. The sterile cover may comprise a first case arranged for covering a front side of the MR device. The first case may comprise a hard case with an embedded clear layer for covering a glass area of the front side of the MR device. The sterile cover may further comprise a second case. The second case may be arranged for covering a headband side of the MR device. The second case may comprise a stretchable case for allowing a flexible adjustment of the headband side of the MR device within the second case.

BRIEF DESCRIPTION OF DRAWINGS

The detailed description is described with reference to the accompanying figures. In the figures, the left-most digit(s) of a reference number identifies the figure in which the reference number first appears. The same numbers are used throughout the drawings to refer like features and components.

DETAILED DESCRIPTION

Some embodiments of the present disclosure, illustrating all its features, will now be discussed in detail. The words "comprising", "receiving", "generating" and other forms thereof, are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a", "an" and "the" include plural references unless the context clearly dictates otherwise. Although any systems and methods similar or equivalent to those described herein can be used in the practice or testing of embodiments of the present disclosure, the exemplary sterile cover for a Mixed Reality (MR) device are now described. The disclosed embodiments of the sterile cover for a Mixed Reality (MR) device are merely exemplary of the disclosure, which may be embodied in various forms.

Various modifications to the embodiment will be readily apparent to those skilled in the art and the generic principles herein may be applied to other embodiments. However, one of ordinary skill in the art will readily recognize that the present disclosure of sterile cover for a Mixed Reality (MR) device is not intended to be limited to the embodiments illustrated, but is to be accorded the widest scope consistent with the principles and features described herein.

MR devices are based on a concept of Mixed Reality (MR). Mixed Reality is the use of both Virtual Reality (VR) and Augmented Reality (AR) technologies to create an environment where physical and virtual objects can exist and interact in real-time. MR devices may be used in medical industry for providing virtual assistance to medical practitioners in surgeries. Typically, virtually assisted surgeries have a major concern related to sterility of head-mount MR devices such as Microsoft HoloLens, Magic Leap 1 Lightware for repeated use. Generally, maintaining sterility of the MR devices is challenging, as the MR devices are exposed to the surgical environment, leading to contamination, wear and tear of the MR devices.

The present subject matter overcomes the problems of the conventional systems. The present subject matter relates to a sterile cover for a Mixed Reality (MR) device. The sterile cover may comprise a first case arranged for covering a front side of the MR device. The first case may comprise a hard case with an embedded clear layer for covering a glass area of the front side of the MR device. Further, the sterile cover may also comprise a second case. The second case may be arranged for covering a headband side of the MR device. Further, the second case may comprise a stretchable case for allowing a flexible adjustment of the headband side of the MR device within the second case.

The sterile cover disclosed in the present subject matter acts as a protective and sterile barrier for the MR device. The sterile cover provides protection against contamination due to physical touch by a user, physical damage such as scratches, or wear and tear of the MR device. Further, the stretchable case of the sterile cover provides flexible adjustment of the MR device without obstructing field of vision through the MR device. The design of the sterile cover matches a profile of the MR device, thereby providing provisions for accessing one or more physical controls integrated to the MR device. In addition, the sterile cover is configured to match with a profile of a flip-up feature in the MR device, thereby enabling easy switching between one of a direct view and a digitally superimposed view. It is to be noted that the present subject matter provides solutions and leads to an improvement over the conventional systems.

Referring now to FIGS. 1A, 1B, 1C, 1D, 1E, 1F, 1G, 1H, 1I, and 1J in combination, a sterile cover for a Mixed Reality (MR) device is illustrated, in accordance with an embodiment of the present subject matter.

Figure 2A:
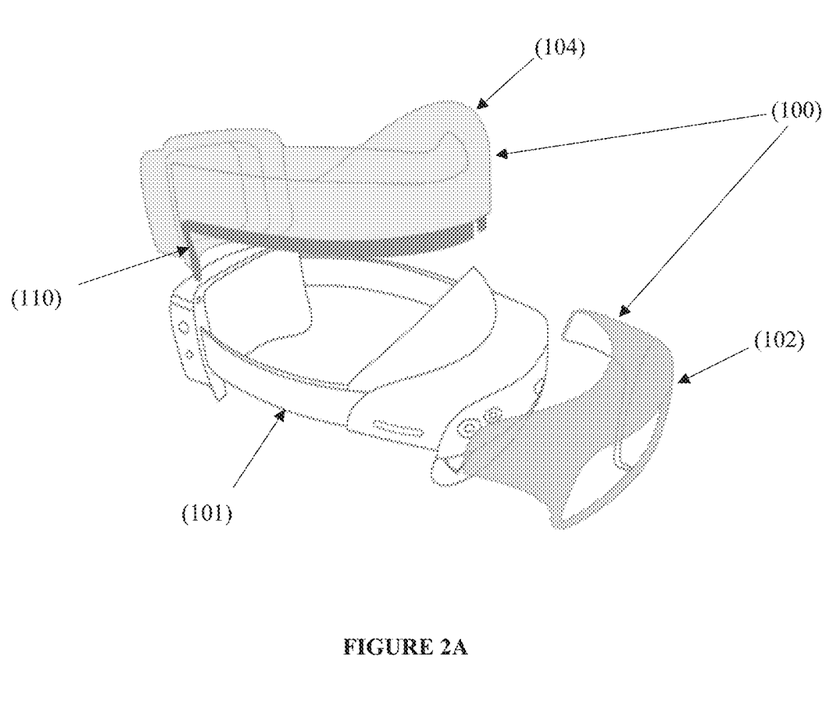
FIG. 2A, FIG. 2B, and FIG. 2C illustrate an exemplary embodiment of the sterile cover for a Mixed Reality (MR) device, in accordance with an embodiment of the present subject matter.
Figure 2B:
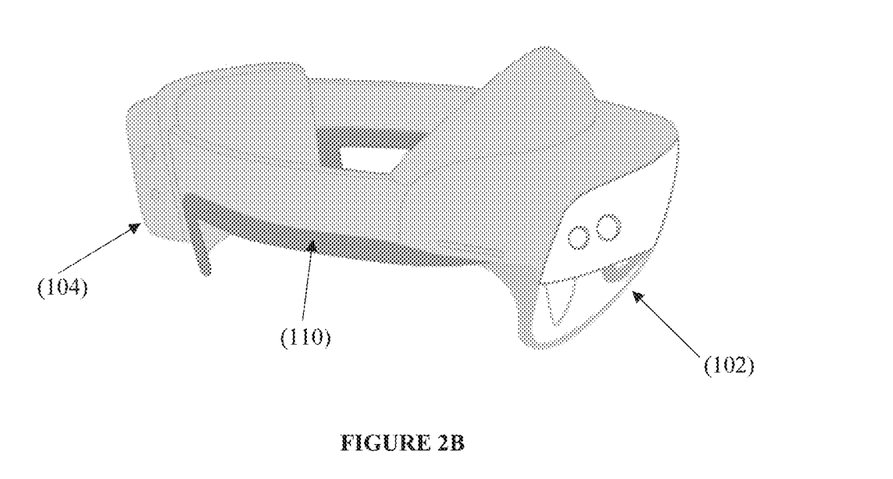
Figure 2C:
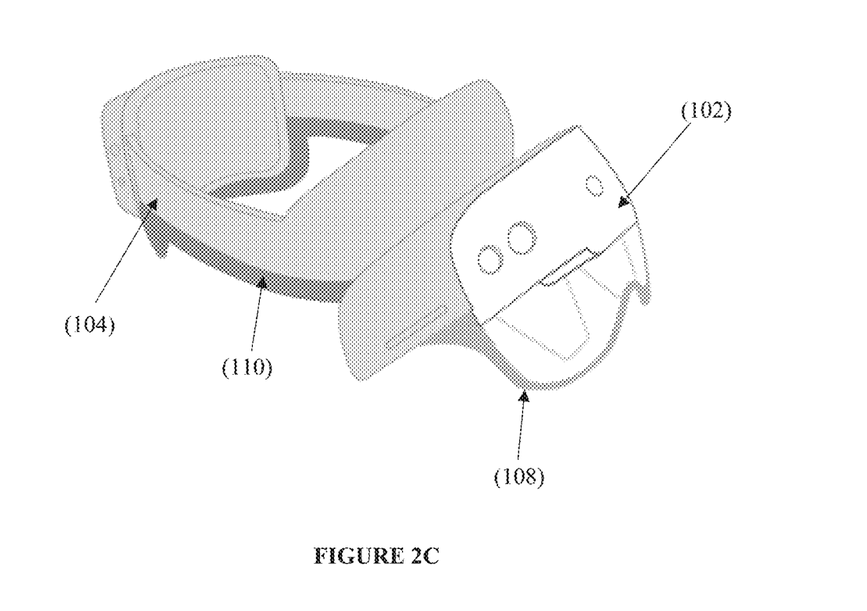

Referring now to FIGS. 2A, 2B, and 2C, an exemplary embodiment of the sterile cover for a Mixed Reality (MR) device is illustrated, in accordance with an embodiment of the present subject matter.

Figure 3A:
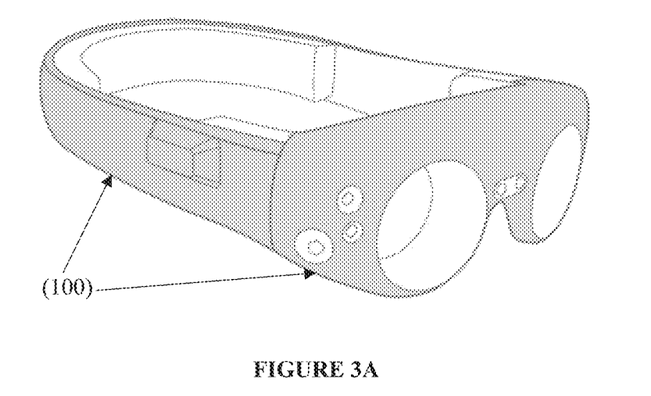
FIG. 3A and FIG. 3B illustrate an exemplary embodiment of the sterile cover for a Mixed Reality (MR) device, in accordance with an embodiment of the present subject matter.
Figure 3B:
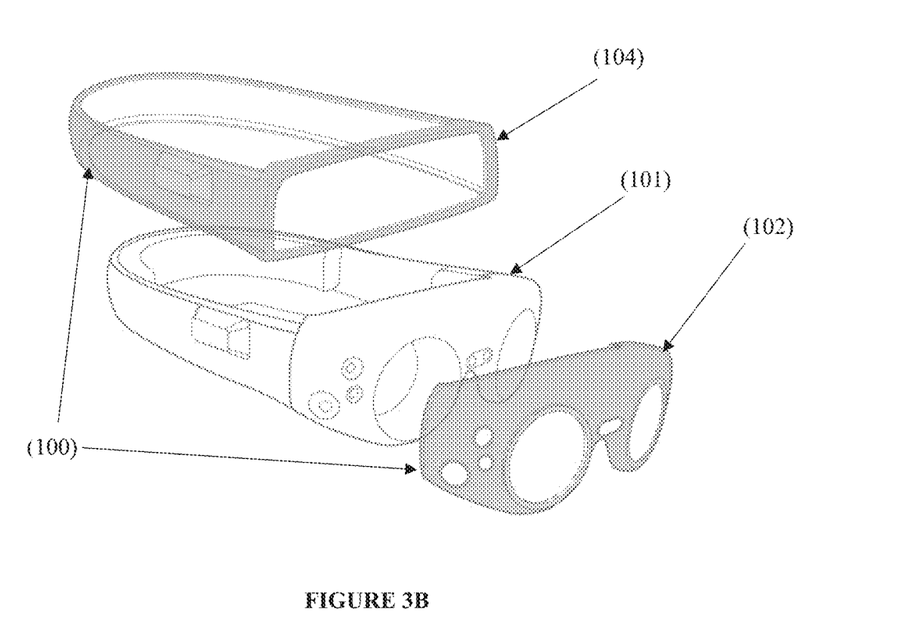

Referring now to FIGS. 3A and 3B, an exemplary embodiment of the sterile cover for a Mixed Reality (MR) device is illustrated, in accordance with an embodiment of the present subject matter.

Further, FIGS. 1A to 1J, 2A to 2C, and 3A to 3B are explained together.

A sterile cover 100 for a Mixed Reality (MR) device 101 is illustrated. The MR device 101 may be a wearable head mounted device including but not limited to, a Microsoft HoloLens (as shown in FIGS. 1A to 1J and 2A to 2C), or a Magic Leap (as shown in FIGS. 3A and 3B). The MR device 101 may be used in one or more application areas including, but not limited to, medical field for performing medical operations. During medical operations, sterilization of the MR device 101 may be challenging. The sterile cover 100 may provide an easy method for re-use of the MR device 101, since the external surfaces and user touchpoints of the MR device 101 may be protected by the sterile cover 100, and acts as a sterile barrier.

Figure 1A:
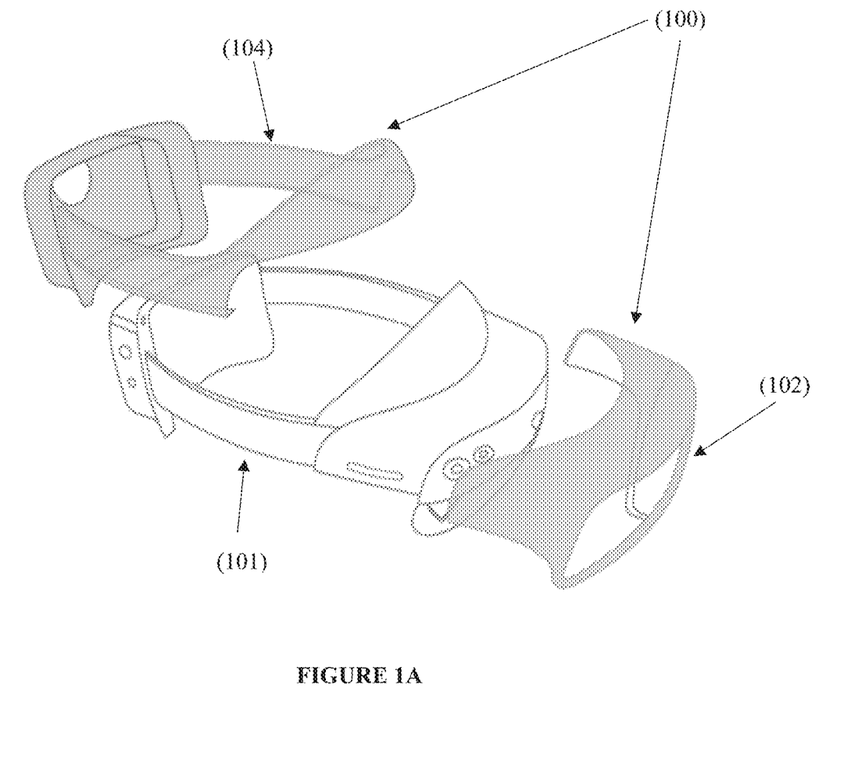
FIG. 1A, FIG. 1B, FIG. 1C, FIG. 1D, FIG. 1E, FIG. 1F, FIG. 1G, FIG. 1H, FIG. 1I, and FIG. 1J illustrate a sterile cover for a Mixed Reality (MR) device, in accordance with an embodiment of the present subject matter.
Figure 1B:
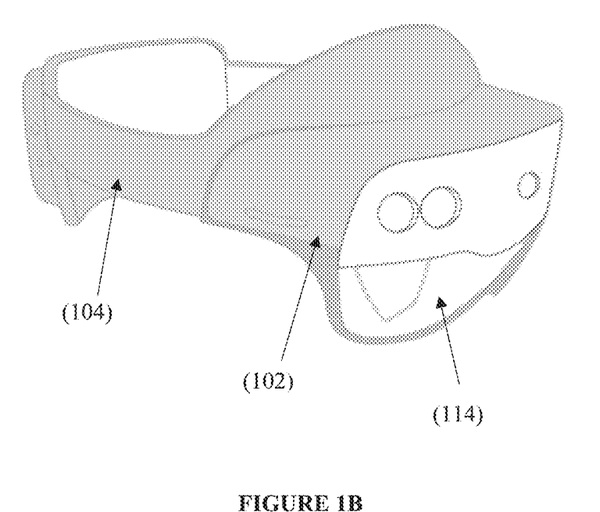

The sterile cover 100 may comprise a first case 102 arranged for covering a front side of the MR device 101 as shown in FIG. 1A. The first case 102 may comprise a hard case with an embedded clear layer 114 for covering a glass area or viewing lenses provided on the front side of the MR device 101 as shown in FIGS. 1A and 1B. The embedded clear layer 114 of the first case 102 is designed in a way to match with a curvature of the glass area providing visibility through the glass area of the MR device 101. The embedded clear layer 114 may comprise one of a clear plastic layer or a glass layer. The embedded clear layer 114 may enable clear visibility through the glass area without any distortion, while acting as a sterile barrier. Also, the embedded clear layer 114 may provide a physical barrier for the glass area against scratches and damages.

In one embodiment, the first case 102 may be configured with one of a transparent, a semi-transparent, an opaque plastic moulded body. The first case 102 may further comprise a clip-on feature in form of one or more mounting points 106 as shown in FIG. 1F to enable an attachment of the first case 102 to the MR device 101. The first case 102 may further comprise a rigid structure over an outer side of the first case 102 for providing protection from physical damage and contamination to the glass area of the MR device 101.

Further, the MR devices 101 may be generally configured with a flip-feature 108 that allows the front side of the MR device 101 to flip-up for enabling direct visibility. The flip-up feature 108 may allow the user to switch between one of a direct view and a digitally superimposed view. In one embodiment, the sterile cover 100 may be configured to match with a profile of the flip-up feature 108 in the MR device 101 as shown in FIGS. 1E and 2C.

The sterile cover 100 may further comprise a second case 104 as shown in FIGS. 1A to 1J, 2A to 2C, and 3A to 3B. The second case 104 may be arranged for covering a headband side of the MR device 101. The headband side of the MR device 101 may be often touched and adjusted for an optimal orientation or tightness of the headband by a user such as a medical practitioner wearing the MR device 101. The second case 104 thus comprises a stretchable case for allowing a flexible adjustment of the headband side of the MR device 101 within the second case 104. The second case 104 may also provide a sterile barrier for the MR device 101 against contamination such as contamination from a surgical environment due to blood splashes, touch of a surgeon's hand or with blood.

In one embodiment, the second case 104 may comprise a silicon cover moulded from soft plastic such as silicon rubber or a flexible plastic film. The stretchable case may allow for expansion or contraction of the headband side by adjusting as per the headband side profile of the MR device 101.

In another embodiment, the second case 104 may comprise a thin plastic cover with a zip-lock feature 110 as shown in FIGS. 2A to 2C. The zip-lock feature 110 may help to hold the thin plastic cover tightly against the headband area.

Figure 1C:
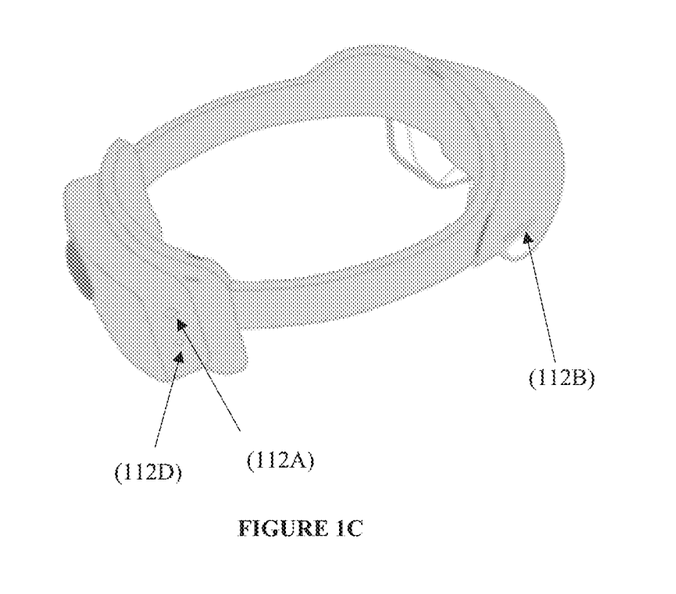
Figure 1D:
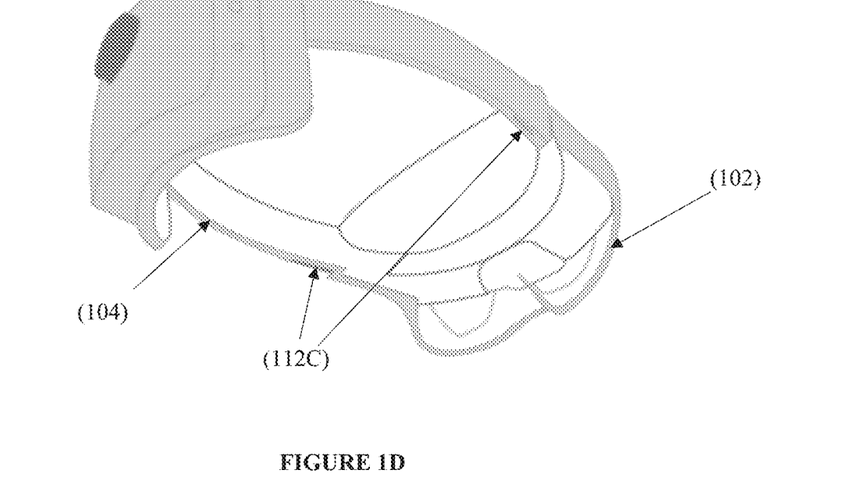
Figure 1E:
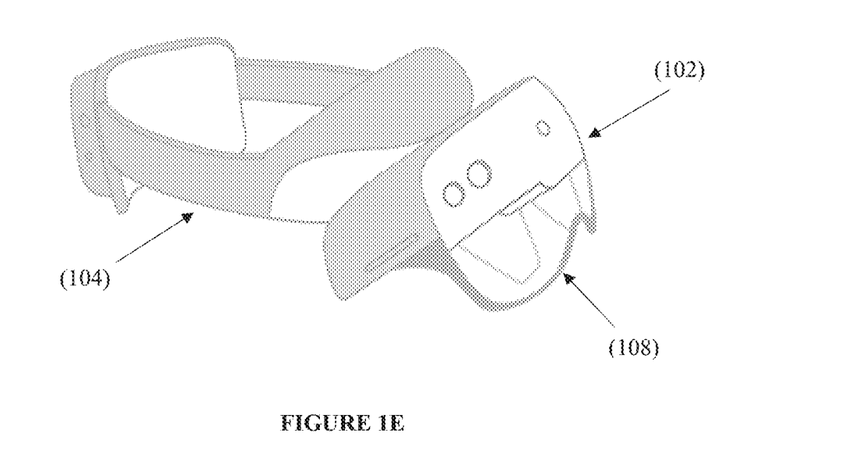
Figure 1F:
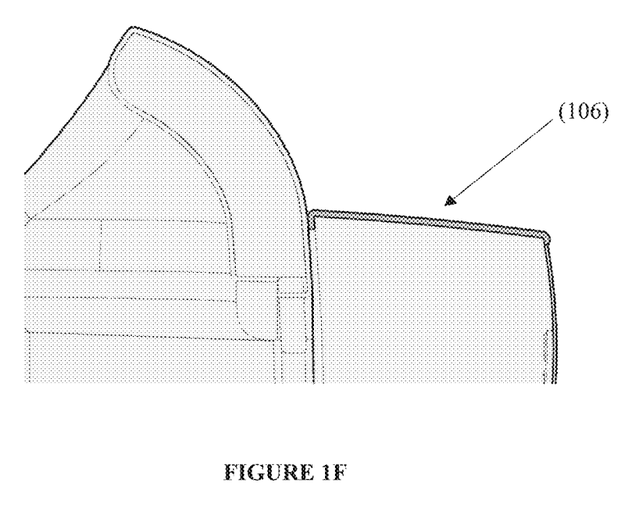
Figure 1G:
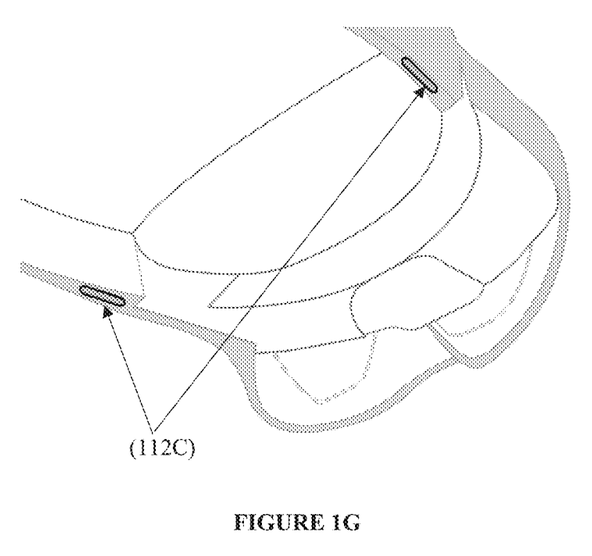
Figure 1H:
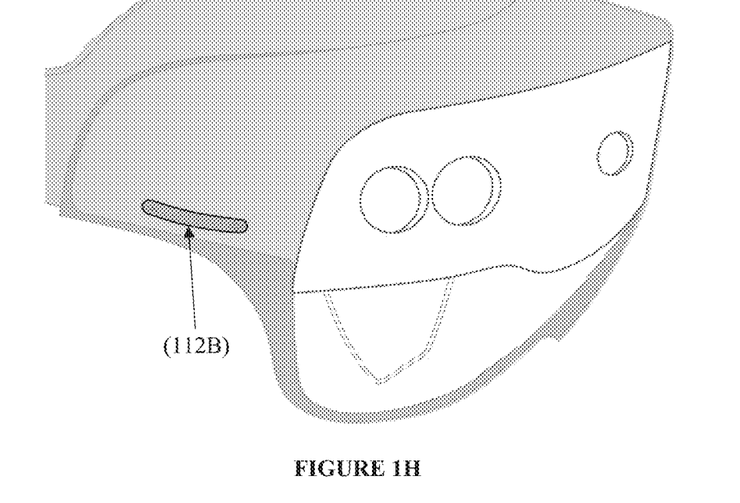
Figure 1I:
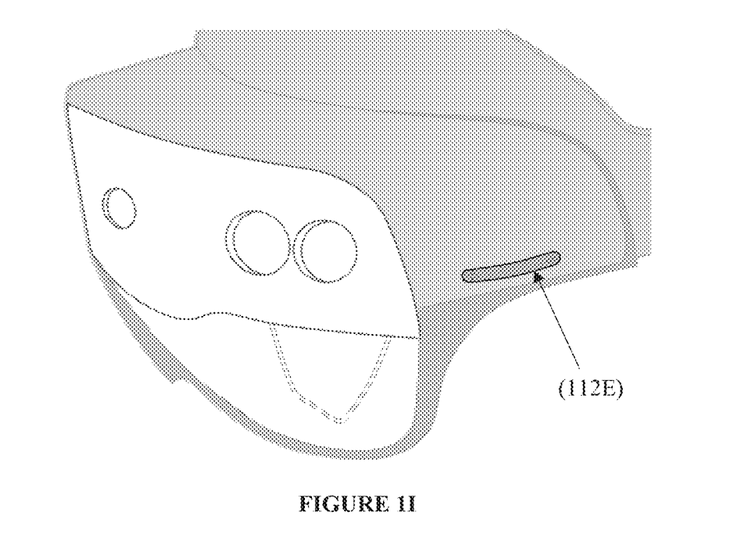
Figure 1J:
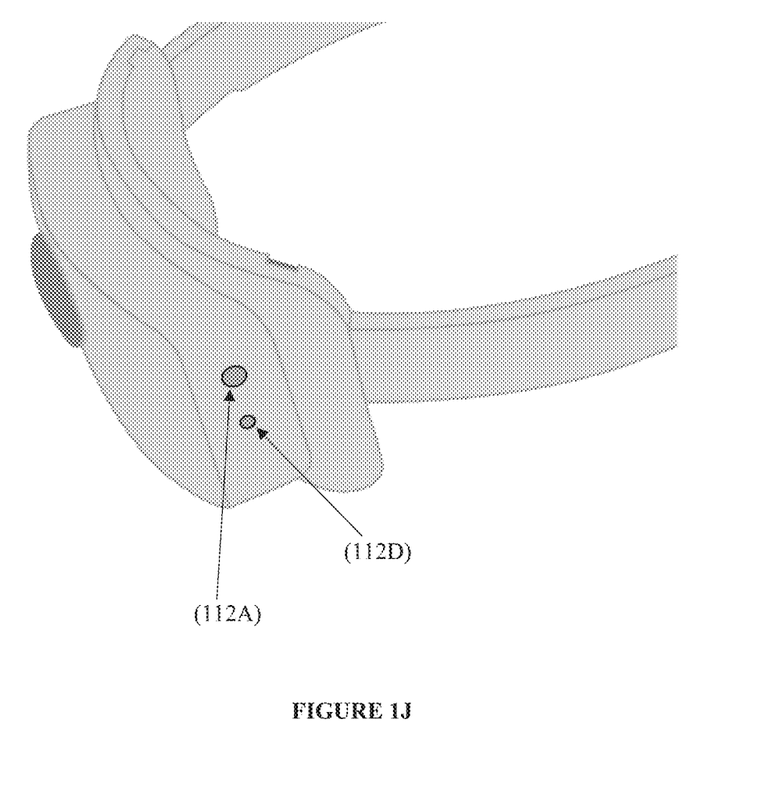

Further, each of the first case 102 and the second case 104 may be provided with provisions for accessing one or more physical controls 112 integrated to the MR device 101 as shown in FIGS. 1C, 1D, 1G, 1H, 1I and 1J. The sterile cover 100 may not obstruct the user from accessing the one or more physical controls 112 while performing the medical operation or any other activity. The one or more physical controls 112 may comprise one or more of a power button 112A, a volume control button 112B, an LED interface 112D, an audio interface, a brightness control button 112E. The audio interface may comprise a mic for providing an input in the form of voice commands. The audio interface may further comprise one or more speakers 112C sealed with waterproof mesh for providing an output in the form of audio as shown in FIGS. 1D and 1G. The audio interface may be protected by the sterile cover 100 acting as the sterile barrier, while preventing the audio from blocking. In addition, the semi-transparent body of the sterile cover 100 may enable light from any LED indicator on the LED interface 112D (as shown in FIGS. 1C and 1J) to pass through the sterile cover 100 for indicating information such battery related information of the MR device 101 etc. Further, the volume control button 112B is shown in FIGS. 1C and 1H. The brightness control button 112E is shown in FIG. 1I. The power button 112A is shown in FIGS. 1C and 1J.

Exemplary embodiments discussed above may provide certain advantages. Though not required to practice aspects of the disclosure, these advantages may include those provided by the following features.

Some embodiments of the sterile cover provide a method for re-use of the MR device for performing medical procedures in a sterile environment.

Some embodiments of the sterile cover provide protection to the MR device from physical damage and contamination due to physical contact of a user.

Some embodiments of the sterile cover provide flexible adjustment of the MR device without obstructing field of vision through the MR device.

Some embodiments of the sterile cover are configured to match with a profile of a flip-up feature in the MR device for enabling switching between one of a direct view and a digitally superimposed view.

Some embodiments of the sterile cover provide provisions for accessing one or more physical controls integrated to the MR device.

Some embodiments of the sterile cover provide secure attachment to the MR device.

Although implementations of a sterile cover for a Mixed Reality (MR) device have been described in language specific to structural features and/or methods, it is to be understood that the appended claims are not necessarily limited to the specific features or methods described. Rather, the specific features and methods are disclosed as examples of implementations of a sterile cover for a Mixed Reality (MR) device.

The invention claimed is:

1. A sterile cover (100) for a Mixed Reality (MR) device (101), the sterile cover (100) comprising:
 a first case (102), arranged for covering a front side of the MR device (101), wherein the first case (102) comprises a hard case with an embedded clear layer (114) for covering a glass area of the front side of the MR device (101); and
 a second case (104) arranged for covering a headband side of the MR device (101), and wherein the second case (104) comprises a stretchable case for allowing a flexible adjustment of the headband side of the MR device (101) within the second case (104)
 wherein the sterile cover (100) is configured to match with a profile of a flip-up feature (108) in the MR device (101), and wherein matching of the sterile cover (100) with the profile of the flip-up feature (108) enables switching of the MR device (101) between one of a direct view and a digitally superimposed view.

2. The sterile cover (100) as claimed in claim 1, wherein each of the first case (102) and the second case (104) are provided with provisions for accessing one or more physical controls (112) integrated to the MR device (101), and wherein the one or more physical controls (112) comprise one or more of a power button (112A), a volume control button (112B), an LED interface (112D), an audio interface (112C), a brightness control button (112E).

3. The sterile cover (100) as claimed in claim 1, wherein the first case (102) is configured with one of a transparent, a semi-transparent, and an opaque plastic moulded body.

4. The sterile cover (100) as claimed in claim 1, wherein the first case (102) comprises a clip-on feature to enable an attachment of the first case (102) to the MR device (101).

5. The sterile cover (100) as claimed in claim 1, wherein the embedded clear layer (114) of the first case (102) matches with a curvature of the glass area providing visibility through the glass area of the MR device (101), and wherein the embedded clear layer (114) comprises one of a clear plastic layer or a glass layer.

6. The sterile cover (100) as claimed in claim 1, wherein the first case (102) comprises a rigid structure over an outer side of the first case (102).

7. The sterile cover (100) as claimed in claim 1, wherein the second case (104) comprises one of a silicon cover, a thin plastic cover with a zip-lock feature (110).

8. The sterile cover (100) as claimed in claim 1, wherein the MR device (101) is a wearable head mounted device comprising one of a Microsoft HoloLens, or a Magic Leap.

* * * * *